United States Patent [19]

Aragona et al.

[11] Patent Number: 5,618,289
[45] Date of Patent: Apr. 8, 1997

[54] INSECT LOCATOR BRUSH

[75] Inventors: James Aragona, North Caldwell; Mark C. Buechel, Livingston, both of N.J.

[73] Assignee: Aragona Buechel Partnership, South Orange, N.J.

[21] Appl. No.: 345,561

[22] Filed: Nov. 8, 1994

[51] Int. Cl.$^6$ ............................ A61B 19/00; A46B 15/00
[52] U.S. Cl. .............................. 606/131; 15/105
[58] Field of Search ............................ 606/131; 119/83, 119/86, 87, 156; 132/120, 126; 15/105

[56] References Cited

U.S. PATENT DOCUMENTS

| | | |
|---|---|---|
| D. 274,658 | 7/1984 | Saferstein et al. . |
| 1,228,669 | 6/1917 | Hardey . |
| 1,259,169 | 3/1918 | Train . |
| 1,909,662 | 5/1933 | Conners . |
| 2,155,299 | 4/1939 | Broyles . |
| 2,384,528 | 9/1945 | Brandt et al. . |
| 2,688,971 | 9/1954 | Daniels et al. . |
| 3,500,034 | 3/1970 | Bissell . |
| 3,655,960 | 4/1972 | Andree . |
| 3,945,717 | 3/1976 | Ryder et al. . |
| 4,225,907 | 9/1980 | Erdell . |
| 4,602,846 | 7/1986 | Karnes ........................... 15/105 |
| 4,671,303 | 6/1987 | Saferstein et al. . |
| 4,988,354 | 1/1991 | Locke . |
| 5,160,194 | 11/1992 | Feldman . |
| 5,196,694 | 3/1993 | Heine et al. . |

Primary Examiner—Robert A. Hafer
Assistant Examiner—Benjamin Koo
Attorney, Agent, or Firm—McGlew & Tuttle

[57] ABSTRACT

An insect locating device includes a support, a brush element connected to the support and a magnification element connected to the support. The magnification element is positioned adjacent to the brush element for viewing a zone adjacent to an area which has been brushed. The support and the brush element include brush connection structure for connecting the brush element to the support and disconnecting the brush element from the support. The support and the magnification element include magnification element connection structure for connecting the magnification element to the support. Illumination structure is also provided, connected to the support for illuminating the viewing zone.

15 Claims, 7 Drawing Sheets

INSECT LOCATOR BRUSH

FIELD OF THE INVENTION

The present invention relates to a device including a brush element for locating ectoparasites that live on or in the skin of a host such as a human or animal.

BACKGROUND OF THE INVENTION

Ectoparasites are organisms that live in or on the skin of a host and derive sustenance from that host. Ectoparasites are a worldwide problem as to health. Problems with ectoparasites result in economic consequences for both human and animal populations.

Ectoparasites include biting or vesicating arthropods and are divided into insect and arachnid groups. Insects include lice, bedbugs, fleas and flies. Arachnids include mites, ticks and spiders.

Ectoparasites transmit various diseases including bacterial, spirochetal, viral, rickettsial, helminthic and protozoal. The following provides an example of ectoparasites and their related diseases:

| Ectoparasite | Disease |
| --- | --- |
| Ticks | |
| Hard Ticks | Hypersensitivity to bites with fever, pruritus and urticaria. |
| | Paralysis |
| | Granuloma |
| | Lyme Disease |
| | Q Fever |
| | Tularemia |
| | Babesiosis |
| | Rocky Mountain Spotted Fever |
| | Ehrlichiosis |
| Soft Ticks | Endemic Relapsing Fever |
| Human Body Lice | Epidemic Relapsing Fever |
| 2 to 4 mm parasites | Epidemic Typhus |
| | Trench Fever |
| Mosquitos | Yellow Fever |
| | Encephalitis |
| | Dengue Fever |
| | Brugia Malayi |
| | Filariasis |
| | Malaria |
| Flies | Leishmaniasis |
| | Onchocerciasis |
| | Trypanosomiasis |
| | Tularemia |
| Fleas and Lice | Murine Typhus |
| | Plague |
| Mouse Mites | Rickettsial Pocks |
| Mites | Scrub Typhus |
| Scabies 0.35 mm organism | |

*Principles and Practice of Infectious Disease*, Third Edition, Mandell, Douglas, Bennett.

Elimination of the various ectoparasites is generally not possible. For example, Lyme disease is carried by what is often referred to as the deer tick. This tick is found in wooded regions wherein there are fairly large populations of deer, rabbits, and other animals. The deer ticks can only be avoided with certainty by staying away from these areas. The areas provide a large reservoir of wild animals that harbor the Lyme disease carrying ticks. Similarly, eradication methods have been relatively unsuccessful in controlling various ectoparasites. Insecticides and environmental manipulation can help to decrease populations of the ectoparasites. However, use of insecticides can have other effects such that the use of insecticides has raised new concerns with regard to resistance to the insecticides by the organisms, environmental damage and personal health concerns with regard to topical insecticides and other agents.

As removing all of the host animals from an area of human and domesticated animal populations is not possible (such as removing all deer and rabbits, etc.), little can be done to fend off diseases carried by ectoparasites, including Lyme disease. Experts have advised that people living in areas wherein particular ectoparasites are present, such as Lyme disease carrying deer ticks, wear clothing so as not to expose skin, and to check for the ectoparasites, after coming in from out of doors. Unfortunately, certain ectoparasites, including deer ticks, are very small.

Deer ticks in their larvae stage are under one half millimeter in size. Similarly, deer ticks in their nymph stage are also small, approximately one half millimeter in size. Detection of these ectoparasites can be quite difficult, particularly detection under human hair, such as ectoparasites which have gotten to human skin, under the cover of human hair, such as the human scalp or the skin of an animal such as a pet.

Removal of the ectoparasite from the skin is always necessary to prevent disease transmittal. As this requires careful and frequent inspection of the skin and hair, the process can be very difficult and time consuming. The process is especially difficult with regard to children, long-haired individuals or restless pets. Parasites, including deer ticks, can be small, hidden in hair and hard to see with the naked eye.

SUMMARY AND OBJECTS OF THE INVENTION

It is an object of the invention to provide a device which improves the ability to detect and remove ectoparasites from the skin, including areas of humans and pets covered by hair.

According to the invention, a device is provided for identifying ectoparasites on or near the skin of their human or animal hosts. The device provides magnification and illumination of a local skin area to assist in identification of the small ectoparasite organism. The device mechanically assists in exposing an area of examination by separating and holding hair away from the field of examination. The device provides magnification and preferably also illumination and provides a field of view wherein access to the skin is provided whereby the offending ectoparasite may be identified and removed.

The device is preferably provided as a modular unit with elements which may be removed for washing and may be substituted for human and animal use. The device includes a brush receiving portion and a brush element which is connectable to the brush receiving portion whereby various different brush elements can be used for different human and animal hair conditions. The brush components are preferably washable and safe for contact on human and animal skin.

The device according to the invention includes a support element including a brush receiving portion. The support element defines a viewing area wherein the brush element, when connected to the support element is adjacent to the viewing area. A magnification element is preferably provided at the viewing area such that the surface of the skin can be examined to detect very small ectoparasites. Most advantageously, the magnification means includes a magnification element for magnifying four times, allowing easy location of ticks, fleas and other ectoparasites. The brush element is connectable to the support via a fixing means to fix the brush in place, adjacent to the viewing area. The brush element preferably includes one of various different brush shapes for a particular application. Most advantageously, the brush is preferably designed with brush bristles which have a natural curve, a curve shape for example generally corresponding to average curvatures of the human head and for example curvatures matching typical animal portions which are to be examined or even other portions of the human body including legs, etc. The positioning of the brush elements, whereby it is received by the support means advantageously allows the support means to be moved through the hair, such as hair on the head of a human, whereby a field of view of the scalp is provided in a region wherein the hair is moved.

The support is preferably is provided with a handle or the like for easy manipulation of the viewing field and for manipulation of the brush element to expose a field of view in an area of hair on the human or animal. The support also preferably includes illumination means for illuminating the exposed field. The illuminating means is preferably positioned adjacent to the magnification means, directed at the viewing region.

The ability to connect the brush to the support means provides various different advantages according to the invention. A plurality of different brushes can be available including brushes with curvatures designed for humans such as brushes with curvatures corresponding to average human head sizes. Brushes can also be provided which have curvatures adapted particularly for pets and the like. A very slight curve can also be provided for large animals and other areas for inspection of humans and animals.

Preferably all components of the device are modular allowing removal of parts for cleaning. The brush elements are removable as noted above and this is particularly useful to clean the brushes for later use. The magnifying element is preferably also removable. This allows cleaning of the magnifying element and also allows replacement. According to a preferred aspect of the invention, the magnifying element is a four times magnifying element. Other degrees of magnification are also possible according to the modular design of the invention.

The bristles of the brush element are preferably blunted or rounded to avoid any damage to the skin or scalp of the pet or human. The bristles are preferably at a height allowing for the use of implements for tick and insect removal. The support preferably has a handle and the handle is preferably right or left-handed allowing engagement of the brush into the hair to expose a viewing region between the person operating the device and the region wherein the hair is engaged by the brush. The handle may further be of a modular design, allowing different handles for use with a single support.

The support is provided with illumination means. This may be in the form of a light directed at the viewing site, in the field of view of the magnification element.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

FIG. 4b is an enlarged view of the detail of I of FIG. 4a;

FIG. 6b is a left side view of the modular magnification element of FIG. 6a;

DETAILED DESCRIPTION OF THE PREFERRED EMBODIMENT

Referring to the drawings in particular, the invention comprises an insect locator brush generally designated 10 including a support portion 12 and a handle part 14. The support part 12 includes brush receiving members 16 which define a brush receiving space 18. A brush element 20 is inserted in the brush receiving space 18. The brush element 20 includes first and second brush engaging elements or brush rails 22. These engaging elements are received in brush support slots 24. The brush receiving elements 22 and the brush support slots 24 cooperate to form brush element connection means. The connection means provides a frictional engagement between the brush receiving portion 16 and the brush element 20.

On a side of the support element 12, opposite the brush receiving space 18, a magnification lens receiving space 26 is provided defined between magnification support elements 28. Each of the magnification lens support elements 28 include magnification lens support slots 30. A magnification lens 32 is provided to be positioned within the magnification lens receiving space 26. The lens 32 includes magnification lens engaging elements or rails 34. The magnification lens engaging elements 34 are designed in a manner similar to the engaging elements 22. This allows the magnification lens 32 to be positioned in the magnification lens receiving space by sliding the magnification lens engaging elements 34 in corresponding slots 30.

The modular construction, wherein the brush element 20 and lens element 32 may be inserted and removed from the brush support 12, allows for ease in cleaning the various elements including the brush 24 and the lens 32. Additionally, the invention provides the ability to use one of a number of different brushes 20. Various different lenses can also be provided however a preferred lens is provided according to the invention with a four times magnification as discussed below.

Figure 1:
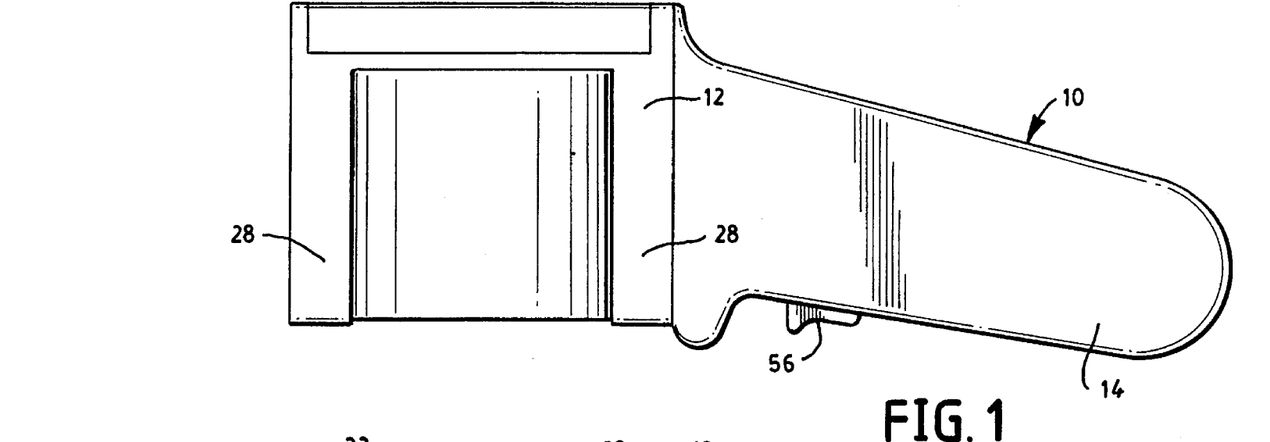
FIG. 1 is a top view of the insect locator device according to the invention.
Figure 2:
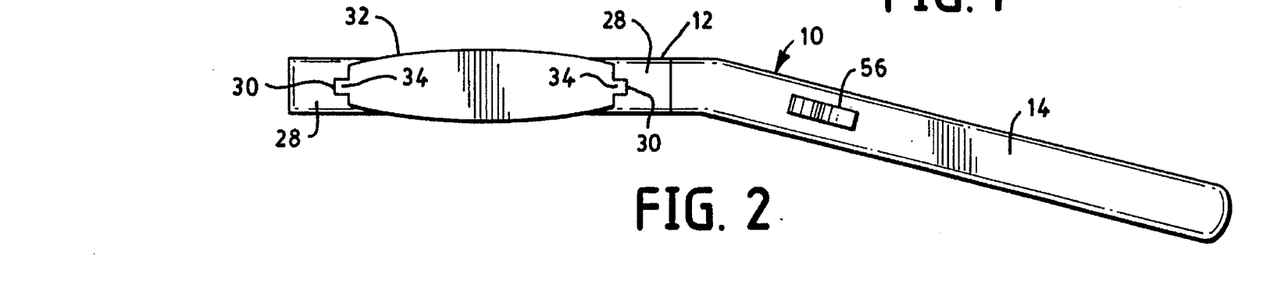
FIG. 2 is a front side view of the device in FIG. 1.
Figure 3:
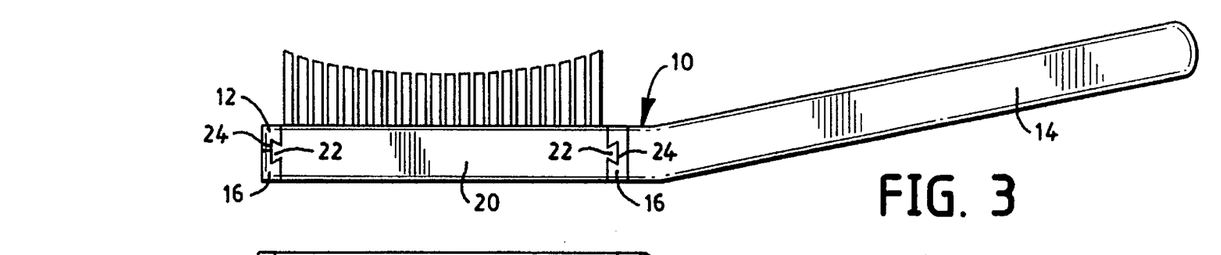
FIG. 3 is a rear side view of the device in FIG. 1.
Figure 4A:
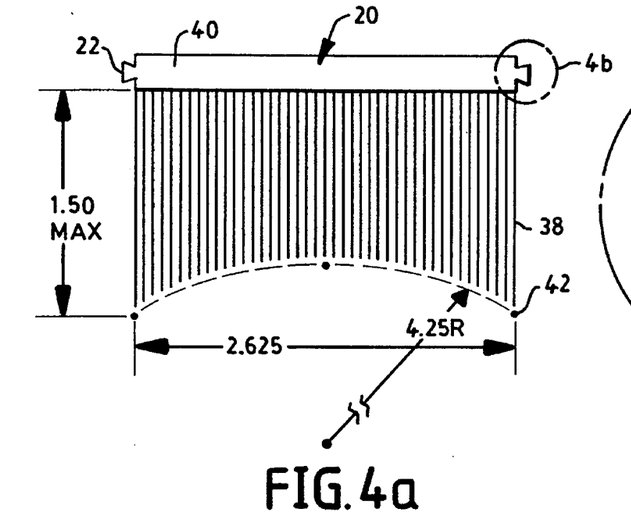
FIG. 4a is a view of a preferred brush element according to the invention with preferred radius of brush bristle ends.
Figure 4B:
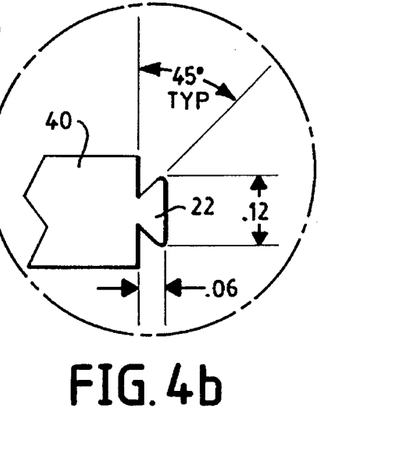
Figure 5A:
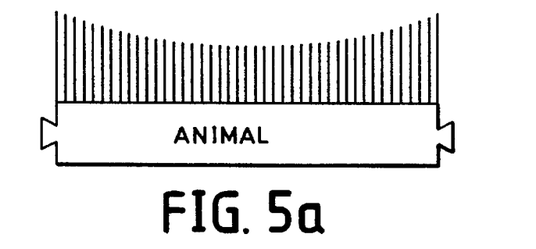
FIGS. 5a, 5b and 5c show the curvature of various different brush bristle ends according to the invention.
Figure 5B:
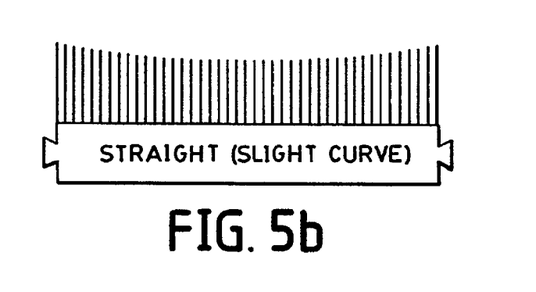
Figure 5C:
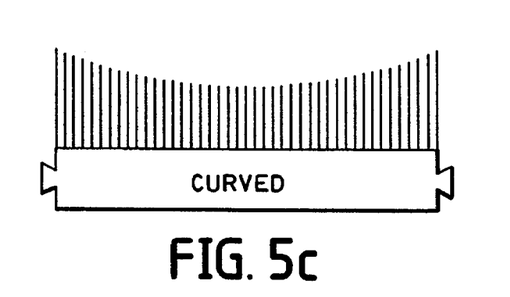

As can be seen in FIG. 4a, the brush element 20 according to the invention has a specific design including a bristles 38 and a base portion 40. The bristles are provided spaced apart as shown to define an animal hair parting and unfolding means. The bristles engage hair of a human or animal for parting the hair or parting the hair and unfolding the hair (including for example uncurling the hair) to expose a region of skin of the human or animal. The bristles 38 preferably have blunted or rounded tips 42 to avoid scratching or abrading the scalp or skin of the animal or human being treated.

Together the bristles 38 if wanted around the tips 42 form non-abrasive human and animal hair parting and unfolding means. Specfically, the structural elements cooperate to unfold and/or part hair for exposing a region as noted above. Further the blunted around the tips form a non-abrasive structure, namely structure for engaging or touching the skin of the human or animal adjacent to the region of skin exposed. This non-abrading skin contact means allows contact with the skin of the human or animal without scratching or braiding the scalp or skin or animal or human being treated.

The invention is most advantageously used for humans, such as to detect deer ticks which pass Lyme disease. As deer ticks can be of a very small size, the location and removal of deer ticks from the scalp of a human can be very problematic.

Figure 9A:
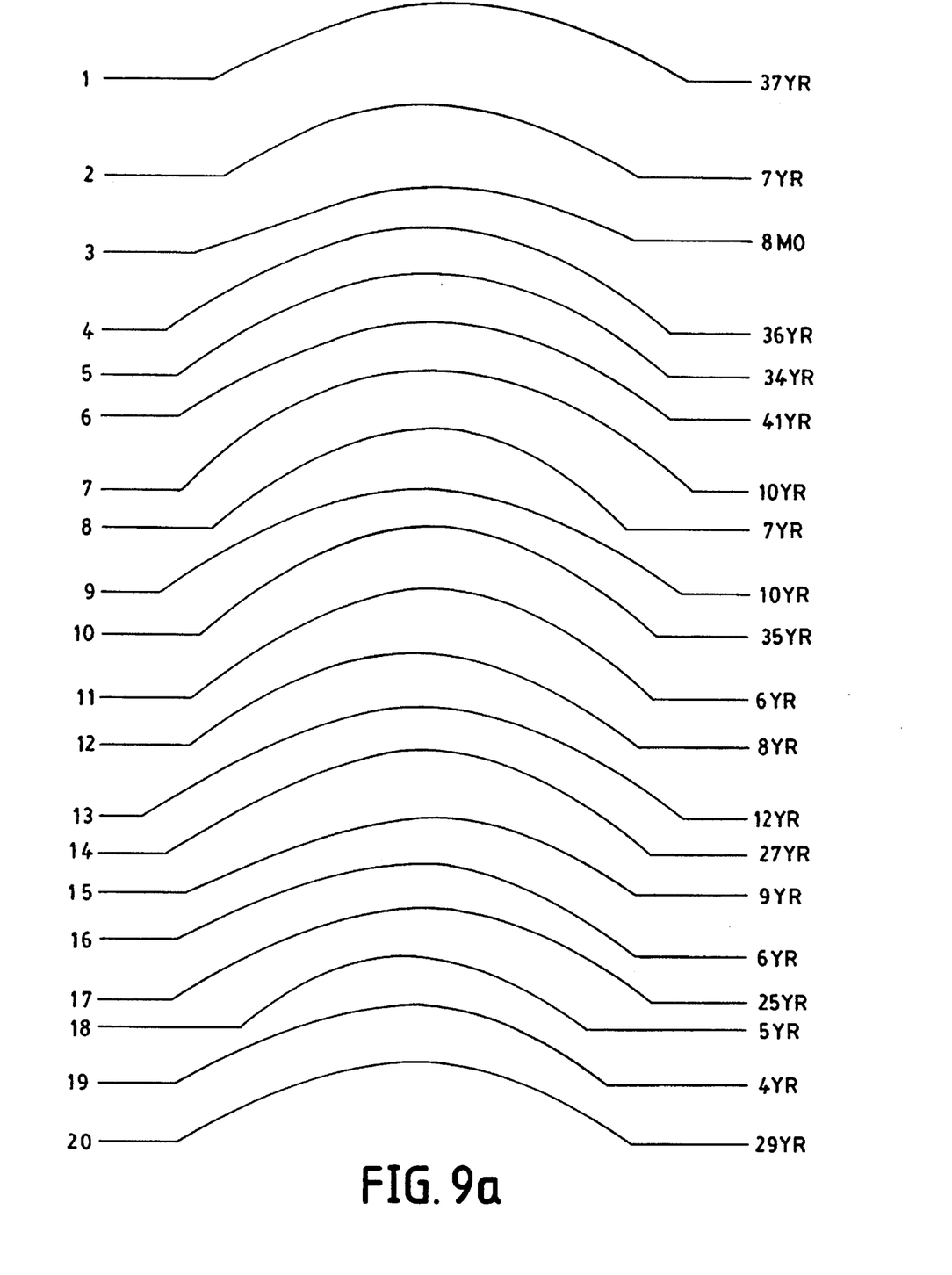
FIG. 9a is a view illustrating the curvature of the head of various individuals.
Figure 9B:
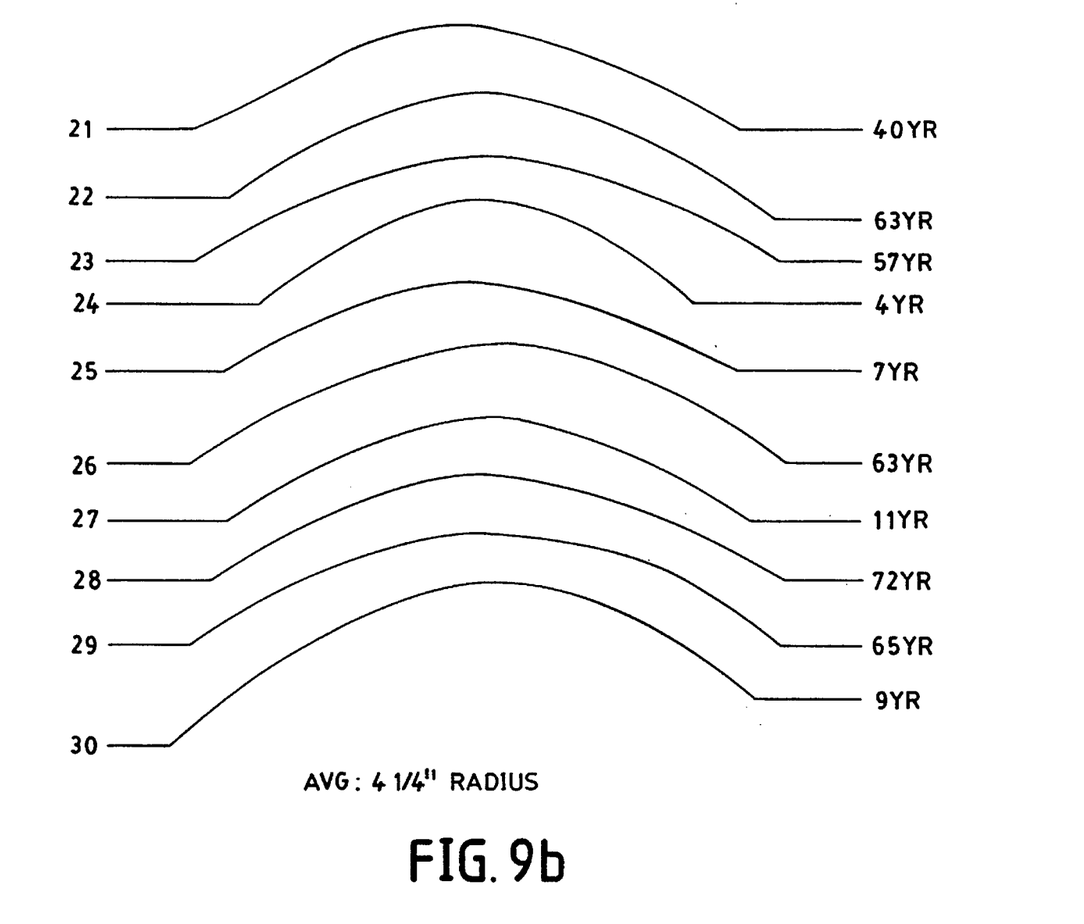
FIG. 9b is a view similar to FIG. 9a, illustrating the curvature of the head of other various individuals.

According to the invention, the curvature of the skull of various humans was analyzed to determine a preferred curvature radius. Specifically, Cranial measurements were made to provide an accurate average or curvature along any plane in the skull. FIGS. 9a and 9b show various cranial measurements. These were analyzed wherein an average was made based on the data as follows:

| SKULL CURVATURES |
| --- |
| 4.25 |
| 4.5 |
| 4.75 |
| 4.25 |
| 4.5 |
| 4.75 |
| 2.5 |
| 4.5 |
| 4.25 |
| 3.25 |
| 3.5 |
| 4 |
| 4.25 |
| 4.5 |
| 4.75 |
| 4.75 |
| 4.25 |
| 4.625 |
| 4.25 |
| 4 |
| 4.75 |
| 2.875 |
| 4.125 |
| 4.25 |
| 4.625 |
| 4.75 |
| 4.625 |
| 4.25 |
| 4.236607 AVERAGE CURVATURE USE 4.25 INCHES |

The brush radius of curvature entails requirements as to the length of the bristles 38. For example, based on the curvature 4.25 inches (radius), the bristle length has an approximate average length of 1.25 inches. The length of the bristles was chosen to be 1¼ inches providing enough space to check the viewing area and providing access to implements for removing an ectoparasite. Further, a magnification of 4 was selected according to a preferred embodiment. This is based on the need to magnify deer ticks and other small ticks which may be quite small as noted above. With a 4 times magnification, these ticks and mites are visible. Although a specific arrangement including bristle length and magnification level have been selected according to a preferred embodiment, both the bristle length and magnification can be provided otherwise according to the invention.

According to the invention, a bi-convex lens is preferably used.

Tick Brush Lens Calculation

Figure 6A:
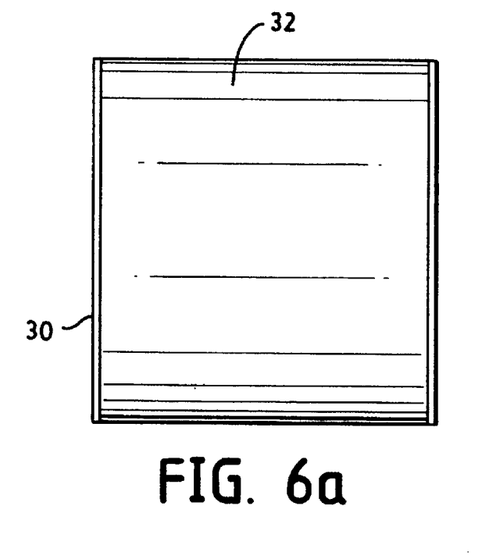
FIG. 6a is a top view of the modular magnification element according to the invention.
Figure 6B:
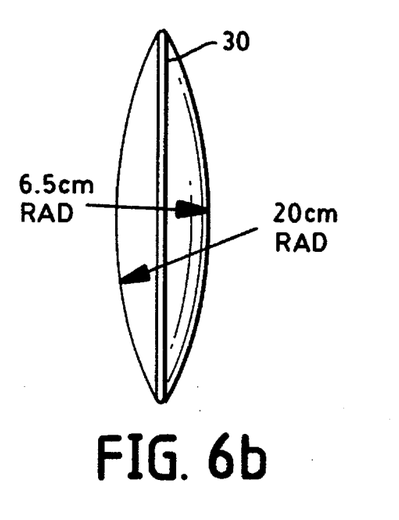
Figure 6C:
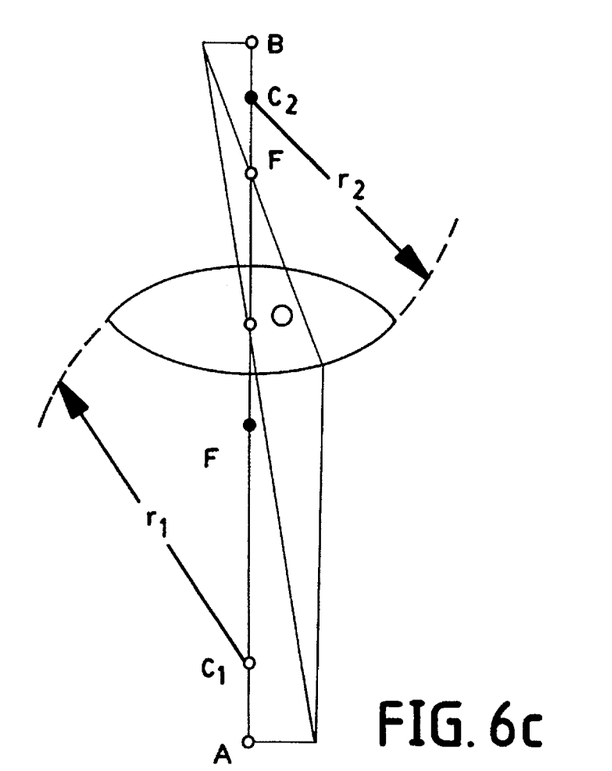
FIG. 6c is a diagrammatical view showing the geometry of the magnification element according to the invention.

Referring to FIG. 6c, the preferred magnification element according the invention is a bi-convex lens based on the following calculation:

The bi-convex lens calculations used are derived from the thin lens derivation. A lens is defined as an optical system which includes two refracting surfaces. The general problem of refraction by a lens is solved by understanding the principles of refraction, whereby the image formed by the first surface serves as the object for the second surface.

Refer to FIG. 10:

From the triangles PBC and P'BC:

$$\phi = \Theta + u \qquad (eq.\ 1)$$

and $$\Theta = u' + \phi' \qquad (eq.\ 2)$$

From Snell's Law:

$$n \sin \phi = n' \sin \phi' \qquad (eq.\ 3)$$

where n and n' are indices at the left and right of a spherical surface.

The image is incident at an angle $\phi$ with the normal, and is refracted at an angle $\phi'$.

For paraxial rays, we may approximate both the sine and tangent of an angle by the angle itself. Then Snell's law becomes:

$$n\phi = n'\phi' \qquad (eq.\ 4)$$

If we combine (eq.1) and eq. 4) we have:

$$\phi = n/n'(u + \Theta) \qquad (eq.5)$$

Substituting into (eq.2) gives:

$$nu + n'n' = (n' - n)\Theta$$

Using the small angle approximations, we obtain:

$$n/s + n'/s' = (n' + n)/R \qquad (eq.6)$$

Very often, the lens is so thin that the thickness, t, is negligible.

Therefore, s1'=(−s2). Since the medium on both sides of the lens is air (index of refraction=1), we obtain:

$$1/sl + n/sl' = (n-1)/R1 \qquad (eq.7)$$

Refraction at the second surface yields the equation:

$$n/s2 + 1/s2' = (1-n)/R2 \quad (eq.8)$$

Adding (eq.7) and (eq.8) yields:

$$1/s1 + 1/s2' = (n-1)(1/R1 - 1/R2) \quad (eq.9)$$

s1 and s2 are set at infinity for thin lenses. Therefore:

$$\frac{1}{f} = (n-1)\frac{1}{R1} - \frac{1}{R1} \quad (eq.\ 10)$$

where:
f=focal length
This equation is called "the lensmaker's equation".
1 Assume a Bi-Convex Lens $$\text{Refraction angle, } n, = \frac{\sin \phi\ i}{\sin \phi\ r} \text{ (Snell's Law)} = 2.962$$

$$\text{Where} \quad r_1 = 6.50 \text{ cm}$$
$$r_2 = 20 \text{ cm}$$

O=Optical Center; Distance=1¼"=3.125 cm=OA
$C_1$, $C_2$=Centers of Curvature
F=Focal Points
$r_1$=Radius of Object Side
$r_2$=Radius of Image Side $$\text{Focal Length} = \frac{1}{OF} = (n-1)\left(\frac{1}{r_1} + \frac{1}{r_2}\right)$$

$$\frac{1}{OF} = (2.962 - 1)\left(\frac{1}{6.5} + \frac{1}{20}\right)$$

$$\frac{1}{OF} = .40 \therefore OF = 2.50 \text{ cm}$$

$$\frac{1}{OB} = \frac{1}{2.50} - \frac{1}{3.125} = -0.08 \therefore OB = -12.50$$

$$\text{Magnification} = -\frac{OB}{OA} = -\left(\frac{-12.50}{3.125}\right) = 4.00$$

Positive #, ∴ Image is Not Reversed,

FIG. 6a shows a preferred magnifying glass element 32 designed to provide a 4.00 magnification factor. This lens is provided with first and second magnification lens engaging elements 30. FIG. 6b shows the preferred curvature of the lens to achieve the magnification factor as noted above. The first lens portion preferably has a curvature based on a 6.5 centimeter radius and the second lens portion has a curvature based on a 20 centimeter radius, calculated as noted above.

Figure 7:
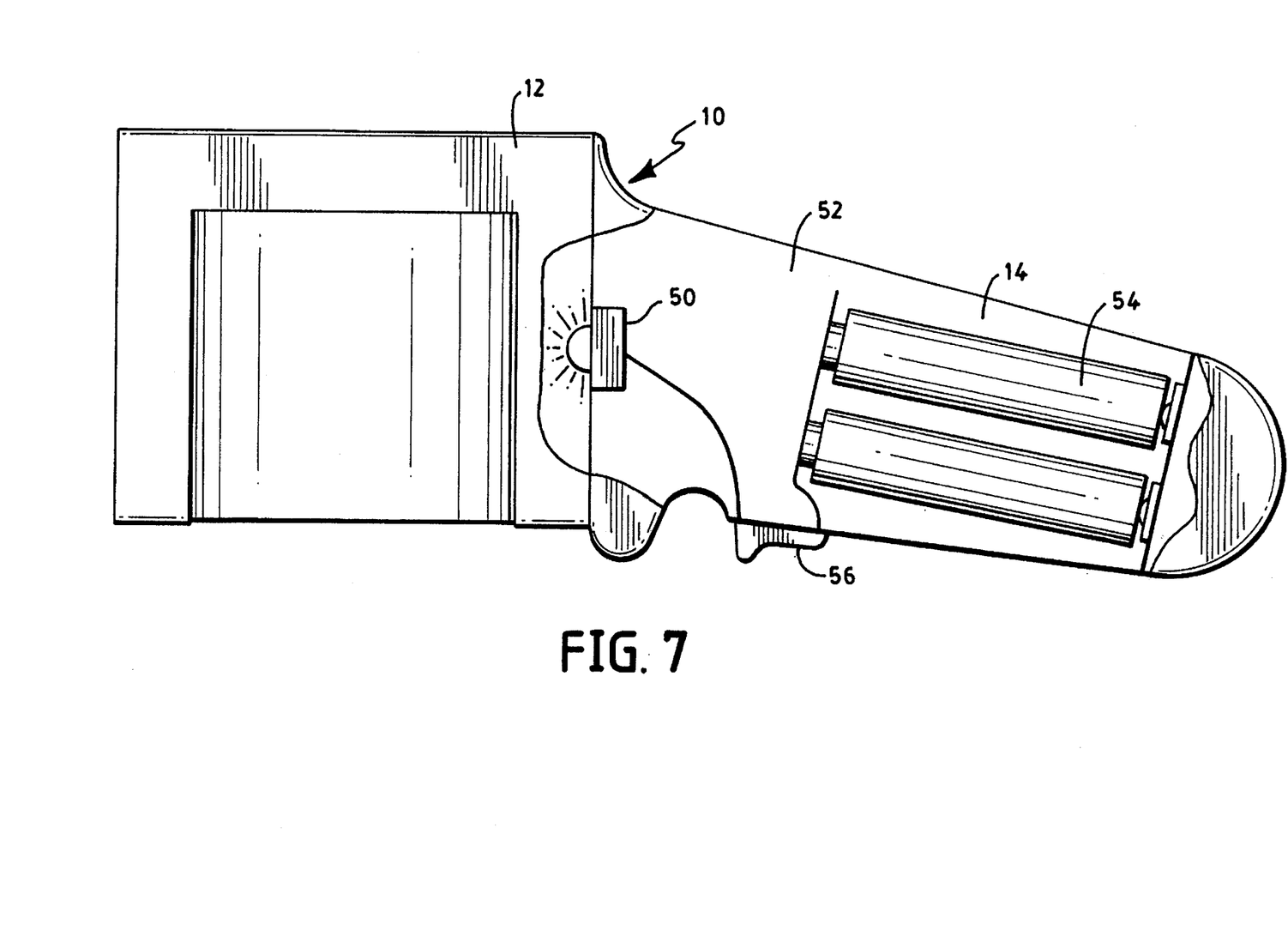
FIG. 7 is a top partially cut away view of the insect locator brush showing a preferred layout of the power source and illumination structure.

As can be seen in FIG. 7, the invention further includes an illumination structure, preferably provided on a lower portion of the support 12. The illumination element 50 is provided in a recessed portion of the lower side of the support 12. The illumination element is simply located to provide a focus of light based on the distance of the bristles and based on viewing area as discussed above.

Power for the illumination element is preferably provided by forming the handle 14 as a hollow element, preferably with a removable portion 52 for replacing batteries 54. A switching element 56 is connected between the illumination element 50 and the batteries for switching the light of the illumination element on and off.

Figure 8:
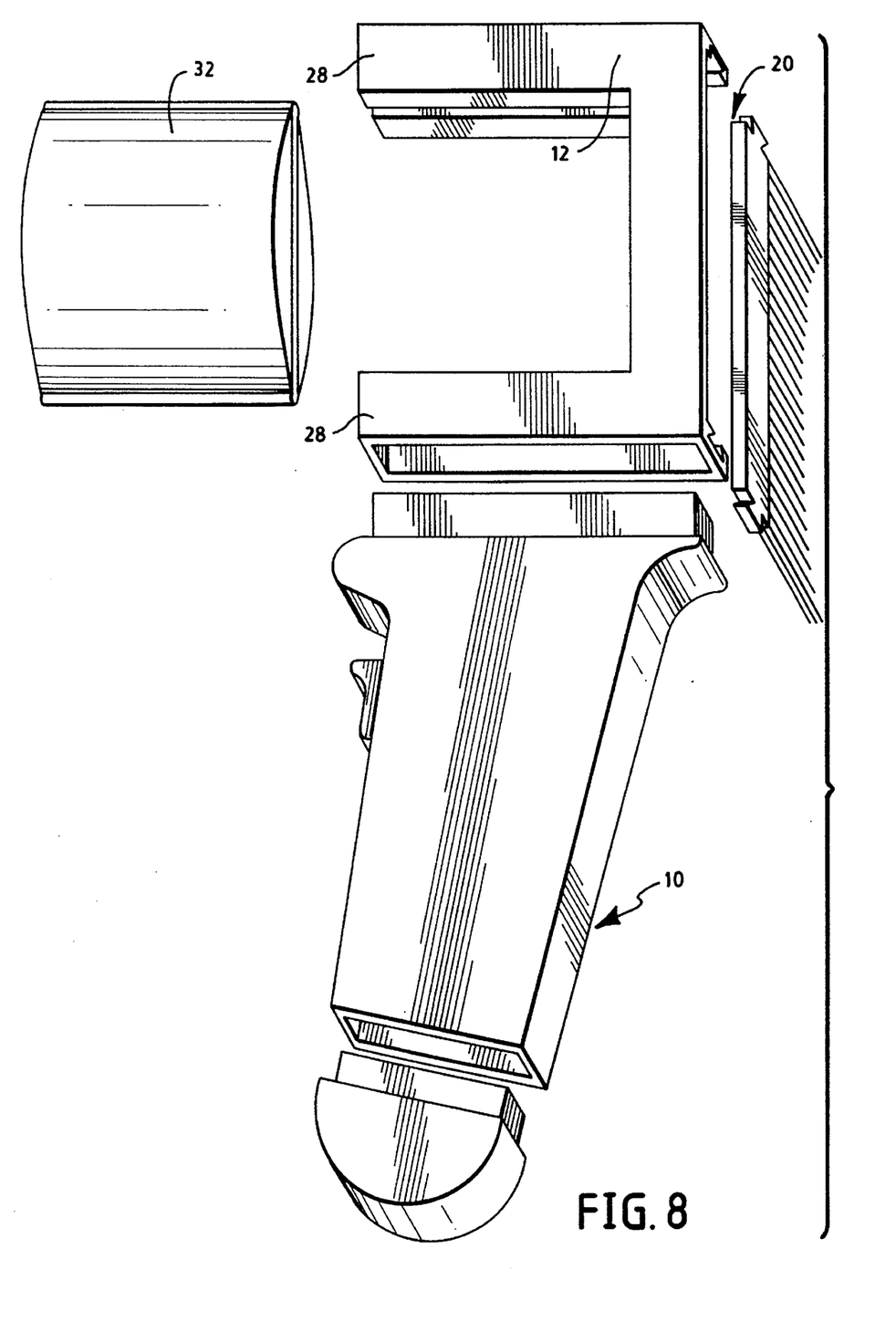
FIG. 8 is a top right perspective exploded view showing the detachment of the various modular units according to the invention.

As shown in FIG. 8, the lens element 32 and the brush element 20 may be removed and reconnected to the support 12 as needed. This allows for cleaning the various elements and also allows for the possibility of replacing one or more of the element. For example, upon damage of one of the brush elements 32 or if the brush element 32 wears out, it can be replaced with a new brush element 32. Further, various different shapes or curvatures of the brush element may be selected based on the application (scalp of a human, dog, cat, etc.). Further, the spacing of the bristles relative to one another may be selected for different types of hair or different types of animal fur. A different magnification element can be provided if the original magnification element is scratched or damaged and a magnification element having a different magnification factor can also be provided if necessary.

While a specific embodiment of the invention has been shown and described in detail to illustrate the application of the principles of the invention, it will be understood that the invention may be embodied otherwise without departing from such principles.

What is claimed is:

1. An insect locating device, comprising:

a support;

non abrasive human and animal hair parting and separating means for engaging hair of a human or animal for separating groups of hair and/or parting the hair of the human or animal to expose a region of skin of the human or animal without abrading the region of skin, said parting and unfolding means being connected to said support;

a magnification element connected to said support, said magnification element being positioned adjacent to said parting and unfolding means for viewing said region; and brush connection means for connecting said hair parting and separating means to said support and disconnecting said hair parting and separating means from said support, said brush connection means including a brush connection rail connected to said hair parting and separating means and a brush connection rail receiving slot associated with said support, said support including a brush receiving space.

2. A device according to claim 1, further comprising:

magnification lens connection means for connecting said magnification lens to said support.

3. A device according to claim 2, wherein said magnification lens connection means includes a magnification lens fixation rail, connected to said magnification lens and a magnification lens receiving slot associated with said support, said support including a magnifcation lens receiving space.

4. A device according to claim 1, further comprising a handle connected to said support.

5. A device according to claim 1, wherein said magnification lens has a 4.0 magnification multiplication factor.

6. An insect locating device, comprising:

a support;

human and animal hair parting and unfolding means for engaging hair of a human or animal for parting the hair or parting the hair and unfolding the hair of the human or animal to expose a region of skin of the human or animal, said hair parting and unfolding means being connected to said support, said hair parting and means including bristles with non abrading skin contact means for contact with the region of skin without abrading the skin;

a magnification element connected to said support, said magnification element being positioned adjacent to said hair parting and unfolding means for viewing a zone adjacent to an area which has been brushed;

illumination means connected to said support, said illumination means directing light toward said zone; and a handle connected to said support, said handle housing a power supply and including a switch connected between said illumination means and said power supply, said switch being activated by a lever positioned on said handle.

7. A device according to claim 6, further comprising: brush connection means for connecting said hair parting and unfolding means to said support and disconnecting said hair parting and unfolding means from said support;

magnification element connection means for connecting said magnification element to said support, said brush connection means including a brush connection rail connected to said hair parting and unfolding means and a brush connection rail receiving slot associated with said support, said support including a brush receiving space.

8. A device according to claim 7, wherein said magnification element connection means includes a magnification element fixation rail, connected to said magnification element and a magnification element receiving slot associated with said support, said support including a magnification element receiving space.

9. An insect locating device, comprising:

a support;

a brush element including bristles said bristles being spaced apart a distance for engaging hair of a human or animal for parting the hair or parting the hair and separating groups of the hair of the human or animal, said brush element being connected to said support;

a hand grip part connected to said support;

a magnification element connected to said support, said magnification element being positioned adjacent to said brush element for viewing said region, said brush element including a plurality of bristles having a curvature defined by longest bristles at an external edge of said brush and shortest bristles in a center of said brush with intermediate bristles having an end position based on a defined radius.

10. A device according to claim 9, wherein said nonabrading skin engaging portions include one of blunted and rounded bristle tips.

11. A device according to claim 10, further comprising:

brush connection means for connecting said brush element to said support and disconnecting said brush element from said support, wherein said brush connection means includes a brush connection rail connected to said brush element and a brush connection rail receiving slot associated with said support, said support including a brush receiving space;

magnification lens connection means for connecting said magnification lens to said support, said magnification lens connection means including a magnification lens fixation rail, connected to said magnification lens and a magnification lens receiving slot associated with said support, said support including a magnification lens receiving space.

12. A device according to claim 9, further comprising illumination means connected to said support, said illumination means directing light toward said region.

13. A device according to claim 9, wherein said defined radius is selected based on a curvature of an average human head.

14. A device according to claim 13, wherein said radius is 4.25 inches.

15. A device according to claim 14, further comprising brush connection means for connecting said hair parting and unfolding means to said support and disconnecting said hair parting and unfolding means from said support.

* * * * *